United States Patent [19]
Burzio et al.

[11] Patent Number: 5,344,581
[45] Date of Patent: Sep. 6, 1994

[54] PROCESS FOR INCREASING THE BLEACHING EFFICIENCY OF AN INORGANIC PERSALT USING AN ACETYLATED MIXTURE OF SORBITAL AND MAMMITOL

[75] Inventors: Fulvio Burzio, Milan, Italy; Roland Beck, Bruxelles, Belgium; Julio Mentech, Lyons, France; Myriam Elseviers, Kampenhout, Belgium

[73] Assignee: Ausimont S.p.A., Milan, Italy

[21] Appl. No.: 922,690

[22] Filed: Jul. 30, 1992

[30] Foreign Application Priority Data

Jul. 31, 1991 [EP] European Pat. Off. ........ 91112870.0

[51] Int. Cl.$^5$ ...................... C11D 3/395; C11D 7/18; C11D 7/26; D06L 3/02
[52] U.S. Cl. ......................................... 252/95; 8/111; 252/99; 252/174.17; 252/174.18; 252/186.38
[58] Field of Search ...................... 252/95, 99, 186.38, 252/174.17, 174.18; 8/111

[56] References Cited

U.S. PATENT DOCUMENTS

| | | | |
|---|---|---|---|
| 2,955,905 | 10/1960 | Davies et al. | 8/111 |
| 3,901,819 | 8/1975 | Nakagawa et al. | 8/111 |
| 4,013,575 | 3/1977 | Castrantas | 252/104 |
| 4,026,798 | 5/1977 | Castrantas | 8/142 |

*Primary Examiner*—Dennis Albrecht
*Attorney, Agent, or Firm*—Bryan Cave

[57] ABSTRACT

The invention relates to a process for increasing the bleaching efficiency of an inorganic persalt and to bleaching and/or detergent compositions suitable for removing stains from textiles or from other products such as paper, cellulose, cork, hair etc. These bleaching and/or detergent and/or anti-incrusting compositions comprise an inorganic persalt and an activating agent comprising an acetylated mixture of sorbitol and mannitol wherein the molar ratio between the bleaching activator and the persalt is usually from 10:90 to 50:50. The bleaching activator having an acetylation degree ranging from 1 to 6 and the weight ratio of sorbitol to mannitol in the mixture is within the range of from 2.5:1 to 4:1.

4 Claims, No Drawings

PROCESS FOR INCREASING THE BLEACHING EFFICIENCY OF AN INORGANIC PERSALT USING AN ACETYLATED MIXTURE OF SORBITAL AND MAMMITOL

The invention relates to a process for increasing the bleaching efficiency of an inorganic persalt and to bleaching and/or detergent compositions suitable for removing stains from textiles or from other products such as paper, cellulose, cork, hair etc.

More particularly, the present invention relates to a process for increasing the bleaching efficiency of an inorganic persalt by adding a bleaching activator based on acetylated polyols, and to bleaching and/or detergent compositions containing said inorganic persalt and bleaching activator.

The inorganic persalts, the bleaching efficiency of which is increased by the process of the present invention, are substances capable of releasing hydrogen peroxide in an aqueous solution. Examples of such inorganic persalts are alkali metal percarbonates, persulfates, persilicates, perpyrophosphates and their mixtures. Preferred alkali metals are sodium, potassium and lithium, particularly sodium.

When an inorganic persalt is used alone it provides a satisfactory bleaching effect at a temperature equal to or higher than 80° C., but at a lower temperature, such as at 40° C. or 60° C., where the washing machines operate, its bleaching efficiency is extremely low.

This property of the inorganic persalt bleaching agents is becoming more and more disadvantageous because of the trend to reduce energy costs by the use of washing machines at low temperature, and because of the introduction of synthetic and coloured fabrics requiring low temperature for washing.

The prior art provides various activating agents for improving bleaching at low temperatures. Such activating agents are e.g. N-acyl compounds such as TAED (tetracetylethylene diamine), acetic acid esters of sugars and polyols such as penta acetyl glucose, octa acetyl sucrose, hexa acetyl sorbitol and hexa acetyl mannitol (U.S. Pat. No.2,955,905, U.S. Pat. No.3,901,819).

The most preferred bleaching activator is TAED leading to very high bleaching. However, TAED has ecological disadvantage since it is a petrochemical, hence, non renewable product.

In comparison with the bleaching activity of TAED, the acetic acid esters of polyols, known as bleaching activators, lead to a lower bleaching. However, said acetic acid esters of polyols have the advantage to be derived from natural and renewable substances.

Therefore, it is an object of the present invention to provide a process for increasing the bleaching of inorganic persalts by the use of such activators which do not possess the above disadvantage of TAED in such a way that their bleaching is high enough.

It has been surprisingly found that an acetylated mixture of sorbitol and mannitol enhances the bleaching efficiency of the inorganic persalts with respect to the individual use of acetylated sorbitol and acetylated mannitol. Thus, a synergistics effect of the acetylated mixture of said sugars has been discovered.

There is no disclosure in the prior art of this synergistic effect.

In accordance with the present invention, a process for increasing the bleaching efficiency of an inorganic persalt is provided wherein an acetylated mixture of sorbitol and mannitol is added to said persalt.

The acetylated mixture according to the present invention, hereinafter referred to as SORMAN, can be prepared by any acetylation process suitable for carbohydrate derivatives such as acid catalysed, alkaline catalysed or organic base catalysed acetylation process, by using as acetylation agent acetic acid, acetic anhydride, acetyl chloride and/or ketene.

The bleaching activator has an acetylation degree ranging from 1 to 6.

The weight ratio of sorbitol to mannitol in the mixture is within the range of from 2,5:1 to 4:1, preferably it is 3:1.

According to a preferred way for the preparation of the acetylated mixture (SORMAN), i.e., the bleaching activator, hydrogenated high fructose corn syrups having a fructose content of 42–55% by weight or hydrogenated invert sugar are acetylated.

SORMAN exhibits a synergistics effect, which property is not common with the simple physical mixture of acetylated sorbitol and acetylated mannitol. The physical mixture shows the additive bleaching effect of each acetylated polyol.

SORMAN according to the invention, furthermore, shows a remarkable reduction of the inorganic incrustation and very efficiently removes blood stains.

The higher the amount of SORMAN (up to the stoichiometric ratio with the persalt) the higher the bleaching efficiency of the activating agent, added to the persalt. Such property, common with the TAED, makes SORMAN particularly suitable for satisfying the requirement of using higher amount of activating agents in the bleaching and/or detergent compositions, aiming to an always increasing bleaching.

Another object of the present invention is bleaching and/or detergent compositions containing an inorganic persalt and an activating agent (SORMAN) comprising an acetylated mixture of sorbitol and mannitol.

SORMAN may be directly added as such to a composition containing the persalt used in the bleaching process. In the case of granular compositions, SORMAN may be added in granular form, showing suitable mechanical features and suitable granulometric distribution. The bleaching and/or detergent compositions containing SORMAN and persalt may also contain other usual components, such as anionic, non-ionic or amphoteric surfactants, alkali metal salts (e.g. sodium carbonate, sodium tripolyphosphate), neutral salts (e.g. sodium sulphate), zeolites, carboxymethyl cellulose, perfumes, enzymes etc.

The molar ratio between the bleaching activator and the persalt usually is from 10:90 to 50:50. When the bleaching efficiency of a persalt is exploited at a low temperature and for a short time, the molar ratio of SORMAN to persalt should preferably be increased.

The following examples are provided for merely illustrative purpose and do not limit in any way the scope of the invention.

SORMAN used in example 1, hereinafter referred to as SORMAN-1 had the composition wherein the weight ratio of hexa acetyl sorbitol to hexa acetyl mannitol was 3:1.

The preparation of SORMAN-1 was carried out as follows: A mixture containing 105 g sorbitol and 35 g mannitol (hydrogenation product obtained from invert sugar) was dissolved in 560 ml acetic anhydride and 280 ml acetic acid. Thereafter 1,4 ml concentrated sulphuric acid was added and the resulting mixture was heated for 2 hours at 100° C. SORMAN-1 was recovered from the acetylation mixture by evaporation and by precipitation in water.

EXAMPLE 1

An automatic washing machine (IGNIS) was made to run under the following conditions:
 washing program at 60° C.;
 linen load: 3 kg cotton swatch (white and clean) per washing cycle;
 6 g SORMAN-1 per washing cycle, corresponding to 4% bleaching activator in the detergent, as reported in Table 1, were added to the following detergent composition (which was also used in all the other examples):

| sodium perborate tetrahydrate: | 30 g/washing |
| detergent base (phosphorous-free, free of bleaching agents) | 114 g/washing |

| Said detergent base contained: | (%) w/w |
| --- | --- |
| overall surfactants (linear sodium dodecylbenzene sulphonate + soap + C13-C15 alcohol, ethoxylated with 7 EO) | 15,4 |
| zeolite (4A) | 28,6 |
| sodium silicate (SiO2/Na2O = 2) | 4,4 |
| sodium carbonate | 16,5 |
| sodium sulfate | 26,5 |
| carboxymethyl cellulose | 1,2 |
| antiincrustation copolymers | 4,8 |
| optical bleaching agents | 0,3 |
| water up to | 100,0 |

For the determination of the bleaching efficiency (bleaching booster activity) the clean linen was washed together with 2 samples (swatches/washing cycle), previously stained in a standard way with red wine by the European Institute of Sankt Gallen (EMPA 114). At the end of each washing cycle said 2 samples were dried and ironed; the whiteness degree was then measured by means of an Elrepho-Zeiss reflectometer. The resulting bleaching percentage (measure of the bleaching efficiency), reported in Table 1, was determined by the formula:

$$\text{bleaching } (\%) = (A-B)/(C-B) \times 100$$

where:
 A = whiteness degree of the swatch after the washing;
 B = whiteness degree of the swatch before the washing;
 C = whiteness degree of the swatch completely bleached.

The whiteness degree of the swatches is expressed as percentage of the whiteness degree of MgO, as standard, when measured with a filter No. 6 (wavelength = 464 nm). The thus obtained percentage (68,0%) is reported in Table 1.

EXAMPLE 2

Example 1 was repeated with the difference that the amount of the bleaching activator SORMAN-1 was 18 g/washing cycle (corresponding to 12% in the detergent) and the amount of sodium sulfate was accordingly reduced in the detergent composition.

The obtained results are reported in Table 1.

EXAMPLES 3 AND 4 (comparative examples)

The bleaching efficiency of TAED was determined according to example 1 by using 6 g/washing cycle (4%) and, respectively, 18 g TAED/washing cycle (12%). The obtained results are reported in Table 1.

EXAMPLES 5 TO 8 (comparative examples)

Examples 1 and 2 were repeated with the difference that SORMAN-1 was replaced by an equal amount of hexa acetyl sorbitol (examples 5 and 6) and, respectively, hexa acetyl mannitol (examples 7 and 8). The results reported in Table 1 clearly show the synergistic effect obtained by the use of SORMAN-1, namely the bleaching activity exhibited by the individually use of acetylated sorbitol and of acetylated mannitol is lower than that obtained by SORMAN-1.

EXAMPLES 9–10 (comparative examples)

Examples 1 and 2 were repeated with the difference that SORMAN-1 was replaced by an equal amount of the physical mixture of hexa acetyl sorbitol and hexa acetyl mannitol wherein the weight ratio of the acetylated sugars was 3:1. The obtained results, reported in Table 1, show that the bleaching efficiency of the physical mixture is lower than that achieved by SORMAN-1 (examples 1 and 2).

EXAMPLE 11

Four automatic washing machines of the Siemens Siwamat Plus 37001 Company were cyclic changed to avoid systematic error and were made to run under the following conditions:
 washing programme at 60° C.,
 linen load: 4,5 kg dirty houshold cloths + test tissues per washing cycle.
 4% SORMAN-1 per washing cycle, as recorded in Table 2, were added to the following detergent composition:
 145,1 g zeolite/polycarboxylate detergent,
 37,8 g perborate tetra hydrate.

For the determination of the bleaching efficiency (bleaching booster activity) the dirty household linen was washed together with 6 standar dirty tissues (in cotton or polyester/cotton) stained with either cacao, tea, coffee, red wine or blood.

At the end of the washing cycle the tissues discharged from the washing machines, were dried and ironed. The obtained bleaching degree was determined according to DIN 44983 T21 by measuring the remission of the washed stained standard tissues.

The results are reported in Table 2.

After 25 washing cycles the loss in tensile strength (%) and, respectively, the inorganic incrustation (%) were determined according to DIN 53 919 T02, DIN 53 857 T01 and, respectively, DIN 44 983 T21. The results are reported in Table 3.

TABLE 1

| Activator amount (g/washing) | 6 (4%) | 18 (12%) |
| --- | --- | --- |
| Activators | Bleaching % | |
| SORMAN-1 (examples 1, 2) | 68,0 | 73,4 |
| TAED (examples 3 and 4) | 69,4 | 76,9 |
| hexa acetyl sorbitol (examples 5 and 6) | 63,7 | 68,0 |
| hexa acetyl mannitol (examples 7 and 8) | 66,9 | 72,0 |
| physical mixture | 66,0 | 68,0 |

TABLE 1-continued (examples 9-10)

TABLE 2

| SORMAN-1 amount (%) | 0 | 4 |
|---|---|---|
| Standard dirty tissues | Remission | |
| Cotton/Cacao (wfk 10F) | 63,2 | 67,4 |
| Cotton/Coffee (wfk 10K) | 79,4 | 81,5 |
| Cotton/Tea (CFT BC-1) | 58,8 | 62,2 |
| Polyester/Cotton/Tea (CFT PC/BC-1) | 49,6 | 54,2 |
| Cotton/Blood (CFT PB) | 68,2 | 71,7 |
| Bleaching intensity | 67 | 74 |

The abbreviations in Table 2, such as wfk 10F, wfk 10K, CFT BC-1 etc. relate to the kind of the standard dirty tissues used in example 11. These standars are produced by "Institute für Angewandte Forschung GmbH" (D-4150 Krefeld 1).

TABLE 3

| SORMAN-1 amount (%) | 0 | 4 |
|---|---|---|

TABLE 3-continued

| Loss in strength (%) | 8 | 6 |
|---|---|---|
| Inorganic incrustation (%) | 4,4 | 1,1 |

We claim:

1. Bleaching and/or detergent and/or anti-incrusting compositions comprising a bleaching activating agent and an inorganic persalt wherein the molar ratio between the activating agent and the persalt is 10:90 to 50:50 and the activating agent comprises a mixture of hexa-acetyl sorbitol and hexa-acetyl mannitol in a weight ratio varying between 2.5:1 and 4.0:1.

2. The composition of claim 1 wherein the weight ratio between hexa-acetyl sorbitol and hexa-acetyl mannitol is about 3 to 1.

3. The composition of claim 1 in which the activating agent mixture is obtained from hydrogenated corn syrup having a fructose content ranging from 42 percent to 55 percent or is obtained from hydrogenated invert sugar.

4. The composition of claim 1 wherein the activating agent is prepared by acetylating a mixture of sorbitol and mannitol.

* * * * *